United States Patent [19]

Pissiotas et al.

[11] Patent Number: 5,135,562
[45] Date of Patent: Aug. 4, 1992

[54] 8-THIA-1,6-DIAZABICYCLO[4.3.0]NONANE HERBICIDES

[75] Inventors: Georg Pissiotas, Lörrach, Fed. Rep. of Germany; Hans Moser, Magden; Hans-Georg Brunner, Lausen, both of Switzerland

[73] Assignee: Ciba-Geigy Corporation, Ardsley, N.Y.

[21] Appl. No.: 672,204

[22] Filed: Mar. 19, 1991

[30] Foreign Application Priority Data

Mar. 22, 1990 [CH] Switzerland ............ 949/90
Mar. 22, 1990 [CH] Switzerland ............ 951/90

[51] Int. Cl.$^5$ .................. A01N 43/82; C07D 513/04; C07C 331/28
[52] U.S. Cl. ......................... 71/90; 544/117; 544/224; 544/229; 544/235; 544/238; 558/17; 558/255; 560/20; 560/47
[58] Field of Search ............ 71/90; 544/229, 235, 544/61, 69, 117

[56] References Cited

U.S. PATENT DOCUMENTS

| | | | |
|---|---|---|---|
| 4,812,161 | 3/1989 | Hagiwara et al. | 71/90 |
| 4,816,063 | 3/1989 | Yamaguchi et al. | 544/224 |
| 4,885,023 | 12/1989 | Yamaguchi et al. | 544/224 |
| 4,906,279 | 3/1990 | Yamaguchi et al. | 544/224 |
| 5,039,331 | 8/1991 | Satow et al. | 544/235 |

FOREIGN PATENT DOCUMENTS 410265 1/1991 European Pat. Off. .

OTHER PUBLICATIONS

Yamaguchi et al., C.A. vol. 107:134316u, p. 725 (1987).

Primary Examiner—Mukund J. Shah
Assistant Examiner—E. Bernhardt
Attorney, Agent, or Firm—Kevin T. Mansfield; Edward McC. Roberts

[57] ABSTRACT

Compounds of formula I

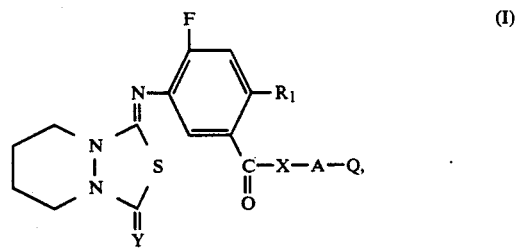

wherein
$R_1$ is halogen;
X is oxygen; or sulfur;
Y is oxygen; or sulfur;
A is a straight-chain or branched $C_1$-$C_4$alkylene chain;
Q is hydroxy; halogen; cyano; unsubstituted or cyano- or halo-substituted $C_2$-$C_6$alkenyl; $C_2$-$C_4$alkynyl; $-CR_2=CH-COOR_3$; $-CH[N(R_2)_2]COOR_2$; $-NR_4(R_5)$; $-CO-NR_6R_7$; $-COON=CR_8(R_8)$; $-C(R_2)(OR_9)_2$; $-Si(R_{10})_3$; $-COOCH_2Si(CH_3)_2-C_1-C_6$alkyl;

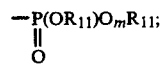

$-CON(R_{12})SO_2-C_1-C_6$alkyl; $-CON(R_{12})SO_2-C_1-C_4$haloalkyl; $C_1-C_6$alkylcarbonyl; $C_2-C_6$alkoxyalkylcarbonyl; benzoyl; benzylcarbonyl; $-COOR_{16}$; $-CO-N(R_2)CH_2-CH_2-CH(O-C_1-C_6$alkyl$)_2$; $-COO(CH_2)_jN(R_2)_2$; $-S(O)_k-R_{14}$; $-S(O)_k-A'-COOR_{13}$; or a five- or six-membered heterocycle containing from 1 to 3 hetero atoms selected from the group N, O and S and bonded via carbon or nitrogen, it being possible for such a heterocycle in turn also to be benzo-fused and to be substituted up to twice by halogen, $C_1-C_4$alkyl, $C_1-C_3$haloalkyl, $C_1-C_3$alkoxy, $C_1-C_3$haloalkoxy, $C_1-C_3$dialkylamino, hydroxy or by carbonyl groups;
have good pre- and post-emergence selective herbicidal and growth-regulating properties.

12 Claims, No Drawings

8-THIA-1,6-DIAZABICYCLO[4.3.0]NONANE HERBICIDES

The present invention relates to novel herbicidally active and plant growth regulating thiadiazabicyclononanes, to processes for their preparation, to novel intermediates, to the compositions comprising the novel compounds as active ingredients, and to their use for controlling weeds, especially selectively in crops of useful plants, or for regulating and inhibiting plant growth.

Thiadiazabicyclononanes having herbicidal activity are known from European Patent Applications Nos. EP-A-0 238 711 and EP-A-0 273 417, but the compounds disclosed therein are not always able to satisfy the requirements as regards potency and selectivity. There is therefore a need for compounds having better activity and greater selectivity.

Novel thiadiazabicyclononanes having improved herbicidal and plant growth regulating activity have now been found.

The thiadiazabicyclononanes according to the invention have the formula I

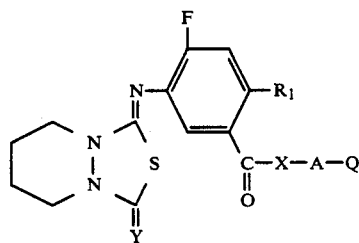

wherein
$R_1$ is halogen;
X is oxygen; or sulfur;
Y is oxygen; or sulfur;
A is a straight-chain or branched $C_1$-$C_4$alkylene chain;
Q is hydroxy; halogen; cyano; unsubstituted or cyano- or halo-substituted $C_2$-$C_6$alkenyl; $C_2$-$C_4$alkynyl; —$CR_2$=CH—$COOR_3$; —CH[N($R_2$)$_2$]COOR$_2$; —NR$_4$($R_5$); —CO—NR$_6$R$_7$; —COON=$CR_8$($R_8$); —C($R_2$)(OR$_9$)$_2$; —Si($R_{10}$)$_3$; —COOCH$_2$Si(CH$_3$)$_2$—$C_1$-$C_6$alkyl;

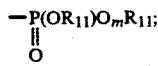

—CON($R_{12}$)SO$_2$—$C_1$-$C_6'$alkyl; —CON($R_{12}$)SO$_2$—$C_1$-$C_4$haloalkyl; $C_1$-$C_6$alkylcarbonyl; $C_2$-$C_6$alkoxyalkylcarbonyl; benzoyl; benzylcarbonyl; —COOR$_{16}$; —CO—N($R_2$)CH$_2$—CH(O—$C_1$-$C_6$alkyl)$_2$; —COO(CH$_2$)$_j$N($R_2$)$_2$; —S(O)$_k$—R$_{14}$; —S(O)$_k$—A'—COOR$_{13}$; or a five- or six-membered heterocycle containing from 1 to 3 hetero atoms selected from the group N, O and S and bonded via carbon or nitrogen, it being possible for such a heterocycle in turn also to be benzo-fused and to be substituted up to twice by halogen, $C_1$-$C_4$alkyl, $C_1$-$C_3$haloalkyl, $C_1$-$C_3$alkoxy, $C_1$-$C_3$haloalkoxy, $C_1$-$C_3$dialkylamino, hydroxy or by carbonyl groups;
$R_2$ is hydrogen; $C_1$-$C_6$alkyl; or $C_2$-$C_6$alkoxyalkyl;
$R_3$ is $C_1$-$C_6$alkyl; or $C_1$-$C_6$hydroxyalkyl;
$R_4$ and $R_5$ are each independently of the other hydrogen; $C_1$-$C_6$alkyl; $C_2$-$C_6$alkoxyalkyl; $C_3$-$C_6$alkenyl; $C_3$-$C_6$alkynyl; $C_3$-$C_6$cycloalkyl; 2-furanylmethyl; 2-tetrahydrofuranylmethyl; 2-(5-methyl)-tetrahydrofuranylmethyl; or 2-thienylmethyl;
$R_6$ and $R_7$ are each independently of the other hydrogen; $C_1$-$C_{12}$alkyl; $C_3$-$C_8$alkenyl; $C_3$-$C_6$alkynyl; $C_2$-$C_8$alkoxyalkyl; $C_1$-$C_4$alkoxy; benzyl; phenyl; or cyano-$C_1$-$C_4$alkyl; or
$R_6$ and $R_7$ together with the nitrogen atom to which they are bonded form a pyrrolidino, piperidino, morpholino, thiomorpholino, 4-methylpiperazino, pyrazolino, imidazolino or 1,2,4-triazoline radical that is unsubstituted or substituted up to twice by $C_1$-$C_4$alkyl;
$R_8$ are each independently of the other $C_1$-$C_6$alkyl; or together form a $C_3$-$C_7$alkylene chain;
$R_9$ are each independently of the other $C_1$-$C_4$alkyl; or $C_1$-$C_4$haloalkyl; or together form an ethano, propano or cyclohexane-1,2-diyl bridge;
$R_{10}$ are each independently of the others $C_1$-$C_6$alkyl; or $C_1$-$C_6$alkoxy;
$R_{11}$ are each independently of the other hydrogen; $C_1$-$C_6$alkyl; $C_1$-$C_6$haloalkyl; cyano-$C_1$-$C_6$alkyl; $C_3$-$C_4$alkenyl; or $C_3$-$C_4$alkynyl;
$R_{12}$ is $C_1$-$C_4$alkyl; or $C_3$-$C_7$cycloalkyl;
A' is a straight-chain or branched $C_1$-$C_4$alkylene chain;
$R_{13}$ is hydrogen; $C_1$-$C_{12}$alkyl; $C_3$-$C_7$alkenyl; $C_3$-$C_6$alkynyl; $C_3$-$C_7$cycloalkyl; $C_2$-$C_8$alkoxyalkyl; $C_3$-$C_5$alkenyloxy-$C_1$-$C_4$alkyl; $C_1$-$C_4$thioalkyl-$C_1$-$C_4$alkyl; or $C_1$-$C_4$dialkylamino-$C_1$-$C_4$alkyl;
$R_{14}$ is $C_1$-$C_{10}$alkyl;

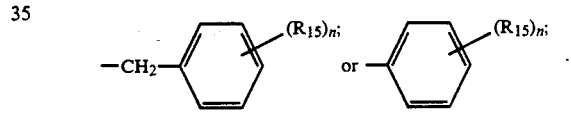

$R_{15}$ is $C_1$-$C_4$alkyl; halogen; or $C_1$-$C_4$alkoxy;
$R_{16}$ is hydrogen; $C_3$-$C_7$alkenyl; $C_3$-$C_6$alkynyl; $C_3$-$C_7$cycloalkyl; $C_2$-$C_8$alkoxyalkyl; $C_3$-$C_5$alkenyloxy-$C_1$-$C_4$alkyl; $C_2$-$C_8$alkylthioalkyl; $C_1$-$C_4$dialkylamino-$C_1$-$C_4$alkyl; or, when $R_1$ is chlorine and Y is oxygen, $C_1$-$C_{10}$alkyl;
j is 0; 2; or 3;
k is 0; 1; or 2;
m is 0; or 1; and
n is 0; 1; 2; or 3;
with the proviso that A is not methano when X is oxygen and Q is hydroxy or halogen.

The compounds of formula I may be asymmetrically substituted by the radicals A and Q. The invention includes both the racemate and the enriched and optically pure forms of the respective stereoisomers.

Unless chiral educts are used, in the processes described in this application the asymmetrically substituted compounds of formula I are generally obtained in the form of racemates. The stereoisomers can then be separated by methods known per se, for example fractional crystallisation after salt formation with optically pure bases, acids or metal complexes, or by chromatographic methods based on physico-chemical properties.

In the above definitions, halogen is to be understood as being fluorine, chlorine, bromine and iodine, preferably fluorine, chlorine and bromine, and especially chlorine and bromine in the case of $R_1$.

A as a $C_1$-$C_4$alkylene chain is methano, ethano (ethane-1,2-diyl), 1-methylethano, 2-methylethano, propano (propane-1,3-diyl), 1-methylpropano, 2-methylpropano, 3-methylpropano, butano and ethane-1,1-diyl. In addition to ethano, preferred alkylene chains are those which are branched in the position adjacent to the substituent X, such as 1-methylethano or 1-ethylethano, but especially ethano and 1-methylethano.

Q as —S(O)$_k$—R$_{14}$ is a thioether (k=0), an R$_{14}$-sulfinyl radical (k=1) or an R$_{14}$-sulfonyl radical (k=2).

In the cases where R$_{14}$ is alkyl, the thioethers are preferred. When R$_{14}$ is an unsubstituted or substituted benzyl or phenyl radical, the sulfonyl structures (k=2) are preferred in addition to the thioethers.

Dialkylamino is preferably dimethylamino, methylethylamino, diethylamino, dibutylamino and diisopropylamino.

Q as a heterocycle includes both unsaturated and completely or partially saturated heterocycles, especially pyridin-2-yl, 1,3-thiazol-5-yl, thiophen-2-yl, pyrrolidin-2-on-1-yl, pyrrolidin-1-yl, morpholin-4-yl, furan-2-yl, indol-1-yl, pyrrol-1-yl, imidazol-1-yl, pyrazol-1-yl and 1,2,4-triazol-1-yl. These heterocycles can in turn be substituted, for example 1-methylpyrazol-4-yl, 5-methylfuran-2-yl, 4-methyl-1,3-thiazol-5-yl or pyrrolidin-2-on-1-yl.

Alkyl is methyl, ethyl, isopropyl, n-propyl, n-butyl, isobutyl, sec-butyl, tert-butyl and the various isomeric pentyl, hexyl, heptyl, octyl, nonyl, decyl, undecyl and dodecyl radicals; preferably methyl, ethyl, isopropyl, n-propyl and n-butyl, Haloalkyl includes, for example, fluoromethyl, difluoromethyl, trifluoromethyl, chloromethyl, dichloromethyl, trichloromethyl, 2,2,2-trifluoroethyl, 2-fluoroethyl, 2-chloroethyl and 2,2,2-trichloroethyl; preferably trichloromethyl, difluorochloromethyl, trifluoromethyl and dichlorofluoromethyl.

Alkoxy is, for example, methoxy, ethoxy, propoxy, isopropoxy, n-butoxy, isobutoxy, sec-butoxy and tert-butoxy; preferably methoxy and ethoxy.

Haloalkoxy is, for example, fluoromethoxy, difluoromethoxy, trifluoromethoxy, 2,2,2-trifluoroethoxy, 1,1,2,2-tetrafluoroethoxy, 2-fluoroethoxy, 2-chloroethoxy and 2,2,2-trichloroethoxy; preferably difluoromethoxy, 2-chloroethoxy and trifluoromethoxy.

Alkylthio is, for example, methylthio, ethylthio, propylthio, isopropylthio, n-butylthio, isobutylthio, sec-butylthio, tert-butylthio or the isomeric pentylthios, preferably methylthio and ethylthio.

$C_2$-$C_8$Alkoxyalkyl or $C_2$-$C_8$alkylthioalkyl are preferably $C_1$-$C_4$alkoxy-$C_1$-$C_4$alkyl or $C_1$-$C_4$alkylthio-$C_1$-$C_4$alkyl, while $C_2$-$C_6$alkoxyalkyl is preferably $C_1$-$C_3$alkoxy-$C_1$-$C_3$alkyl.

Alkenyl is to be understood as being straight-chain or branched alkenyl, for example vinyl, allyl, methallyl, 1-methylvinyl, but-2-en-1-yl, pentenyl, 2-hexenyl or 3-heptenyl. Alkenyl radicals having a chain length of 2 or 3 carbon atoms are preferred. When the alkenyl radical is bonded to a hetero atom (nitrogen, oxygen or sulfur) and is unsubstituted, the alkenyl radical is bonded via a saturated carbon atom.

The alkynyl radicals occurring in the definitions of the substituents may be straight-chain or branched, for example ethynyl, propargyl, 3-butynyl, 1-methylpropargyl, 1-pentynyl or 2-hexynyl. Ethynyl and propargyl are preferred. When the alkynyl radical is bonded to a hetero atom (nitrogen, oxygen or sulfur) and is unsubstituted, the alkynyl radical is bonded via a saturated carbon atom.

Cycloalkyl is, for example, cyclopropyl, dimethylcyclopropyl, cyclobutyl, cyclopentyl, methylcyclopentyl, cyclohexyl or cycloheptyl, but preferably cyclopropyl, cyclopentyl or cyclohexyl.

In substituents that are composed of several basic components, the subsidiary components can be chosen freely within the scope of the definition.

Preference is given to compounds of formula I wherein

R$_1$ is fluorine; chlorine; or bromine;

A is a straight-chain or branched $C_1$-$C_4$alkylene chain;

n is 0; 1; or 2;

Q is $C_1$-$C_{10}$alkylthio; COOR$_{16}$; —S(O)$_k$R$_{14}$; —NR$_4$(R$_5$); a heterocyclic radical that is unsubstituted or substituted up to twice by $C_1$-$C_4$alkyl or once by a carbonyl group and is selected from the group pyridinyl, 1,3-thiazolyl, thiophenyl, pyrrolidinyl, morpholinyl, furanyl, indolyl, pyrazolyl, 1,2-oxazolyl, pyrrolyl, imidazolyl, pyrazolyl and 1,2,4-triazolyl;

R$_4$ and R$_5$ are each independently of the other $C_1$-$C_4$alkyl;

R$_{14}$ is

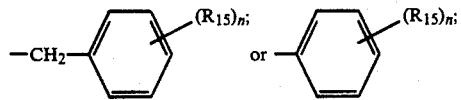

k is 0; 1; or 2;

n is 0; 1; 2; or 3;

R$_{15}$ is $C_1$-$C_4$alkyl; fluorine; chlorine; bromine; or $C_1$-$C_4$alkoxy; and R$_{16}$ is cyclohexyl; $C_1$-$C_4$alkoxy-$C_1$-$C_4$alkyl; $C_1$-$C_4$alkylthio-$C_1$-$C_4$alkyl; $C_1$-$C_4$dialkylamino-$C_1$-$C_4$alkyl; or, when R$_1$ is chlorine and Y is oxygen, $C_1$-$C_{10}$alkyl.

Special preference is given to compounds of formula I wherein

R$_1$ is chlorine; or bromine;

A is ethano; 1-methylethano; 2-methylethano; methano; or propano;

Q is $C_1$-$C_5$alkylthio; COOR$_{16}$; —S(O)$_k$R$_{14}$; pyridin-2-yl; 1,3-thiazol-5-yl; thiophen-2-yl; pyrrolidin-2-on-1-yl; pyrrolidin-1-yl; morpholin-4-yl; furan-2-yl; indol-1-yl; pyrrol-1-yl; imidazol-1-yl; pyrazol-1-yl; 1,2,4-triazol-1-yl; 4-methyl-1,3-thiazol-5-yl; or 5-methylfuran-2-yl;

k is 0; 1; or 2;

R$_{14}$ is benzyl; or phenyl;

R$_{16}$ is cyclohexyl; $C_1$-$C_4$alkoxy-$C_1$-$C_4$alkyl; $C_1$-$C_4$alkylthio-$C_1$-$C_4$alkyl; $C_1$-$C_4$dialkylamino-$C_1$-$C_4$alkyl; or, when R$_1$ is chlorine and Y is oxygen, $C_1$-$C_{10}$alkyl.

Within the scope of the compounds of formula I and of the preferred and especially preferred ranges special mention should be made of those compounds of formula I wherein a) X is oxygen;
b) Y is oxygen;
c) A is —CH$_2$—CH$_2$—;
d) A is

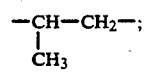

e) A is

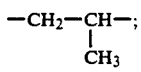

f) Q is $C_1$-$C_5$alkylthio;

g) Q is —$NR_4(R_5)$ and $R_4$ and $R_5$ are each independently of the other $C_1$-$C_4$alkyl;

h) $R_1$ is chlorine or bromine;

i) $R_1$ is chlorine;

j) X is sulfur, Y is oxygen and Q is $COOR_{16}$;

k) A is —$CH_2$—;

l) A is —$CH_2$—$CH_2$—$CH_2$—.

The invention relates also to compounds of formula Ia

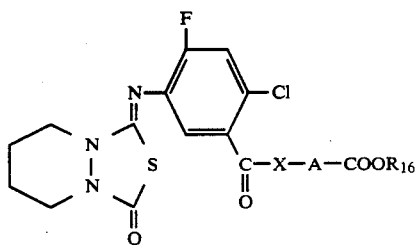

wherein

X is oxygen or sulfur;

A is a straight-chain or branched $C_1$-$C_4$alkylene chain and $R_{16}$ is $C_1$-$C_{10}$alkyl.

Especially good activity is exhibited by compounds of formula Ia wherein A is m) —$CH_2$—$CH_2$—;

n) 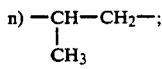

o) 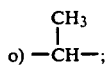

p) 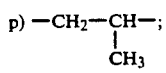

q) —$CH_2$—; or r) —$CH(CH_3)$—.

Of those groups of compounds of formula Ia, prominence is given especially to those wherein X is oxygen; or sulfur; especially sulfur;

A is 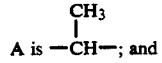; and $R_{16}$ is $C_1$-$C_6$alkyl.

In addition compounds of formula Ia are of interest, wherein

X is oxygen; or sulfur; especially oxygen;

A is $CH_2$; and $R_{16}$ is $C_1$-$C_6$alkyl.

Compounds that should be given specific mention are especially:

9-[4-chloro-2-fluoro-5-(methoxycarbonylmethylthiocarbonyl)-phenylimino]-8-thia-1,6-diazabicyclo[4.3.0]nonan-7-one, 9-[4-chloro-2-fluoro-5-(1-methoxycarbonyl-ethylthiocarbonyl)-phenylimino]-8-thia-1,6-diazabicyclo[4.3.0]nonan-7-one, 9-[4-chloro-2-fluoro-5-(methoxycarbonylmethylthiocarbonyl)-phenylimino]-8-thia-1,6-diazabicyclo[4.3.0]nonan-7-one and 9-[4-chloro-2-fluoro-5-(methoxycarbonylmethoxycarbonyl)-phenylimino]-8-thia-1,6-diazabicyclo[4.3.0]nonan-7-one.

The invention relates also to compounds of formula Ib

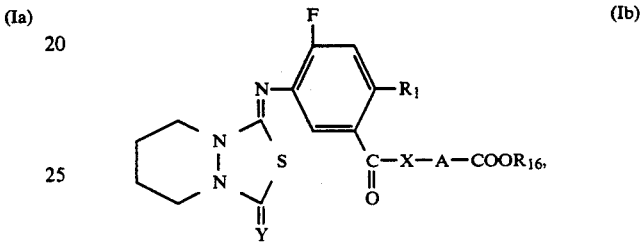

wherein

Y is oxygen;

X is oxygen or sulfur;

A a $C_1$-$C_2$alkylene chain; and $R_{16}$ is $C_1$-$C_4$alkoxy-$C_1$-$C_4$alkyl; or $C_1$-$C_4$alkylthio-$C_1$-$C_4$alkyl.

Of the compounds of formula Ib, special mention should be made of those subgroups wherein a) A is —$CH_2$—;

b) A is —$CH_2$—$CH_2$—; or c) A is —$CH(CH_3)$—.

Especially preferred individual compounds of formula Ib that may be mentioned are:

9-[4-chloro-2-fluoro-5-(2-methoxy-ethoxycarbonylmethylthiocarbonyl)-phenylimino]-8-thia-1,6-diazabicyclo[4.3.0]nonan-7-one (Comp. No. 1.49), 9-[4-chloro-2-fluoro-5-(2-methoxy-1-methyl-ethoxycarbonylmethylthiocarbonyl)-phenylimino]-8-thia-1,6-diazabicyclo[4.3.0]nonan-7-one (Comp. No. 1.51), 9-[4-chloro-2-fluoro-5-(2-methoxy-1-methyl-ethoxycarbonyl-1-ethylthiocarbonyl)-phenylimino]8-thia-1,6-diazabicyclo[4.3.0]nonan-7-one (Comp. No. 1.55), 9-[4-chloro-2-fluoro-5-(2-methoxy-ethoxycarbonyl-1-ethylthiocarbonyl)-phenylimino]-8-thia-1,6-diazabicyclo[4.3.0]nonan-7-one (Comp. No. 1.54) and 9-[4-chloro-2-fluoro-5-(2-ethoxy-ethoxycarbonylmethylthiocarbonyl)phenylimino]-8-thia-1,6-diazabicyclo[4.3.0]nonan-7-one (Comp. No. 1.52).

9-[4-Chloro-2-fluoro-5-(2-methoxy-ethoxycarbonyl-1-ethylthiocarbonyl)-phenylimino]-8-thia-1,6-diazabicyclo[4.3.0]nonan-7-one (Comp. No. 1.54) is especially outstanding.

The invention relates also to compounds of formula Ic,

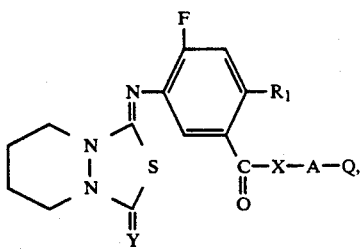

(Ic)

wherein
Y is oxygen;
X is oxygen; or sulfur;
R₁ is chlorine;
A is a $C_1$-$C_2$alkylene bridge; and
Q is a 5- or 6-membered heterocycle having from 1 to 3 hetero atoms selected from the group N, O and S and bonded via carbon or nitrogen, it being possible for such a heterocycle in turn also to be benzo-fused and to be substituted up to twice by halogen, $C_1$-$C_4$alkyl, $C_1$-$C_3$haloalkyl, $C_1$-$C_3$alkoxy, $C_1$-$C_3$haloalkoxy, $C_1$-$C_3$dialkylamino, hydroxy or by carbonyl groups.

The invention relates especially to compounds of formula Ic wherein
Y is oxygen;
X is oxygen;
A is —CH₂—; —CH₂—CH₂—; or —CH(CH₃)—; and
Q is a heterocyclic radical that is unsubstituted or substituted up to twice by $C_1$-$C_4$alkyl or once by a carbonyl group and is selected from the group pyridinyl, 1,3-thiazolyl, thiophenyl, pyrrolidinyl, morpholinyl, furanyl, indolyl, pyrazolyl, 1,2-oxazolyl, pyrrolyl, imidazolyl, pyrazolyl and 1,2,4-triazolyl.

Especially preferred individual compounds of formula Ic that may be mentioned are:
9-{4-chloro-2-fluoro-5-[2-(4-methyl-thiazol-5-yl)-ethoxycarbonyl]-phenylimino}-8-thia-1,6-diazabicyclo[4.3.0]nonan-7-one (Comp. No. 1.21) and
9-{4-chloro-2-fluoro-5-[2-(pyridin-2-yl)-ethoxycarbonyl]-phenylimino}-8-thia-1,6-diazabicyclo[4.3.0]nonan-7-one (Comp. No. 1.20).

The invention relates also to compounds of formula Id

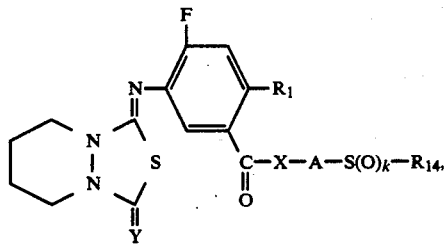

(Id)

wherein
Y is oxygen;
X is oxygen; or sulfur;
R₁ is chlorine;
A is a $C_2$-$C_4$alkylene bridge;
k is 0; and
R₁₄ is $C_1$-$C_{10}$alkyl;

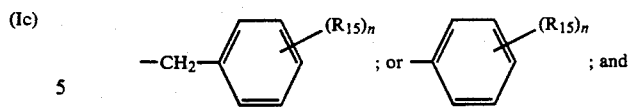

$R_{15}$ is $C_1$-$C_4$alkyl; halogen; or $C_1$-$C_4$alkoxy.

The invention relates especially to compounds of formula Id wherein
X is oxygen;
A is —CH(CH₃)—CH₂—; or —CH₂—CH₂—;
k is 0;
R₁₄ is $C_1$-$C_6$alkyl; or

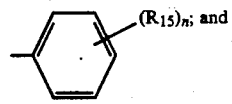

$R_{15}$ is $C_1$-$C_4$alkyl; halogen; or $C_1$-$C_4$alkoxy.

Especially good activity is exhibited also by compounds of formula Id wherein A is

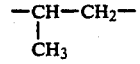

and Q is $C_1$-$C_5$alkylthio. Of those compounds special preference is given to those wherein X and Y are oxygen.

The following compounds of formula Id may be mentioned specifically:
9-[4-chloro-2-fluoro-5-(2-methylthio-1-methylethoxycarbonyl)-phenylimino]-8-thia-1,6-diazabicyclo[4.3.0]nonan-7-one (Comp. No. 1.02),
9-[4-chloro-2-fluoro-5-(2-ethylthio-1-methylethoxycarbonyl)-phenylimino]-8-thia-1,6-diazabicyclo[4.3.0]nonan-7-one (Comp. No. 1.03),
9-[4-chloro-2-fluoro-5-(2-propylthio-1-methylethoxycarbonyl)-phenylimino]-8-thia-1,6-diazabicyclo[4.3.0]nonan-7-one (Comp. No. 1.04),
9-[4-chloro-2-fluoro-5-(2-isopropylthio-1-methylethoxycarbonyl)-phenylimino]-8-thia-1,6-diazabicyclo[4.3.0]nonan-7-one (Comp. No. 1.05),
9-[4-chloro-2-fluoro-5-(2-n-butylthio-1-methylethoxycarbonyl)-phenylimino]-8-thia-1,6-diazabicyclo[4.3.0]nonan-7-one (Comp. No. 1.06),
9-[4-chloro-2-fluoro-5-(2-phenylthio-ethoxycarbonyl)-phenylimino]-8-thia-1,6-diazabicyclo[4.3.0]nonan-7-one (Comp. No. 1.16) and
9-[4-chloro-2-fluoro-5-(2-p-chlorophenylthio-1-methylethoxycarbonyl)-phenylimino]-8-thia-1,6-diazabicyclo[4.3.0]nonan-7-one (Comp. No. 1.56).

The compounds of formula I are prepared by converting an isothiocyanato-benzoic acid ester of formula II

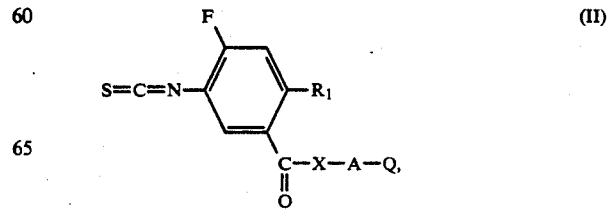

(II)

wherein R₁, X, A and Q are as defined under formula I, with hexahydropyridazine into the compound of formula III

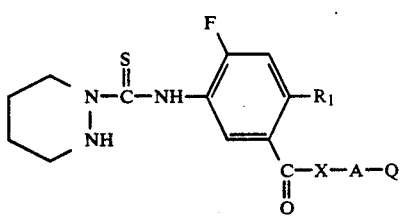
(III)

which is then reacted in the presence of a base with a compound of formula IV

CYCl₂     (IV), wherein Y is oxygen or sulfur.

The isothiocyanato-benzoic acid esters of formula II and the thioureas of formula III are novel. They are valuable intermediates for the preparation of the end products according to the invention. This application relates also to those intermediates.

The isothiocyanato-benzoic acid esters of formula II

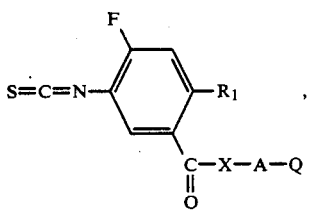
(II)

can be prepared by reaction of an aniline of formula X

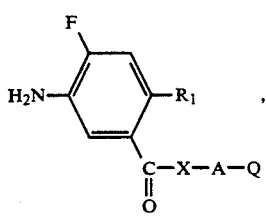
(X)

wherein R₁, X, A and Q are as defined above, with thiophosgene.

The reaction of the benzoic acid esters of formula II with hexahydropyridazine is advantageously carried out in an inert solvent at temperatures of from −5° C. to the boiling temperature of the solvent, especially from 0° to +50° C., preferably at room temperature. Suitable solvents for this reaction are, for example, toluene, xylene, ethyl acetate or acetonitrile.

The reaction of the compound of formula III with the compound of formula IV is advantageously effected in an inert solvent at low temperatures, preferably at from 0° to +50° C., especially from 0° to +15° C. Suitable bases for this reaction are, for example, pyridine, triethylamine or N,N-dimethylaniline.

Suitable solvents are, for example, 1,2-dichloroethane, dichloromethane or toluene.

In accordance with a further process, the compounds of formula I can be prepared by reaction of a compound of formula VI

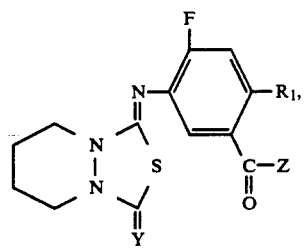
(VI)

wherein R₁ and Y are as defined under formula I and Z is a nucleofugal group, such as chlorine, bromine, azido or —O—CO—C₁-C₄alkyl, or is OH, with an alcohol or thiol of formula VII

H—X—A—Q     (VII)

wherein X, A and Q are as defined under formula I.

An esterification reaction can be used also to prepare compounds of formula I'

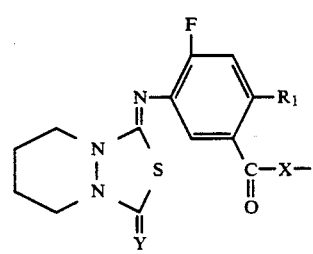
(I')

wherein the radicals X, Y, R₁, R₁₆ and A are as defined under formula I, by reaction of a carboxylic acid derivative of formula VIII

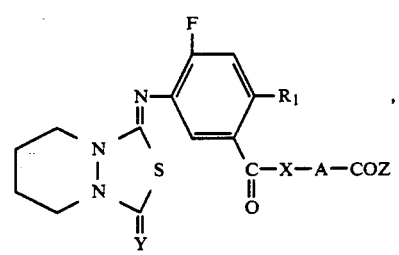
(VIII)

wherein the radicals X, Y, R₁ and A are as defined under formula I and Z is a nucleofugal group, such as chlorine, bromine, azido or —O—CO—C₁-C₄alkyl, or is OH, with an alcohol or thiol of formula IX

HO—R₁₆     (IX)

wherein R₁₆ is as defined under formula I.

The esterification of the acids VI or VIII (Z=OH) is carried out with acid catalysis in an inert solvent or directly in the alcohol or thioalcohol VII. In the esterification of the acid derivatives of formulae VI or VIII in which Z is a nucleofugal group, the addition of a catalytic or equimolar amount of a base is advantageous. Such esterification reactions are familiar to the person skilled in the art.

The alcohols of formulae VII and IX are known or can be prepared analogously to processes known in the literature. In particular, the alcohols VII in which Q is a heterocycle can be prepared by reduction of the corresponding carboxylic acids, aldehydes or ketones or by the addition of the heterocycle to correspondingly substituted oxiranes. Reference is made especially to the following literature for the preparation of these alcohols:

Pyridines: E. Brown (Ed.), *The Chemistry of Heterocyclic Compounds*, Vol. 14, part 4: Pyridine and its Derivatives, J. Wiley and Sons, 1964, pages 2 to 100.

1,3-Thiazoles: J. P. Aune in *The Chemistry of Heterocyclic Compounds*, Vol. 34, part 1: Thiazole and its Derivatives, J. Wiley and Sons, 1979, pages 452 to 459.

Thiophenes: G. Masumarra in *The Chemistry of Heterocyclic Compounds*, Vol. 44, part 3: Thiophene and its Derivatives, J. Wiley and Sons, 1986, pages 975 to 1131.

Pyrrolines: H. J. Anderson and C. E. Loader in *The Chemistry of Heterocyclic Compounds*, Vol. 48: Pyrroline and its Derivatives, J. Wiley and Sons, 1990, pages 398 to 483.

1,2,4-Triazoles: C. Temple in *The Chemistry of Heterocyclic Compounds*, Vol. 37: 1,2,4-Triazole and its Derivatives, J. Wiley and Sons, 1981, pages 3 to 29 and *Beilsteins Handbuch der Organischen Chemie* (Beilstein's Handbook of Organic Chemistry), Vol. 26$^{III/IV}$, pages 36 to 326.

Imidazoles: K. Hofmann (Ed.) *The Chemistry of Heterocyclic Compounds*, Vol. 6: Imidazole and its Derivatives, J. Wiley and Sons, 1953, pages 340 to 360; *Beilsteins Handbuch der Organischen Chemie*, Vol. 23$^{III/IV}$ page 571.

Furanes: *Rodd's Chemistry of Carbon Compounds*, Vol IV, Part A, pages 109 ff, Elsevier Sci. Publ. Comp. Amsterdam 1973.

Morpholines: *Beilsteins Handbuch der Organischen Chemie*, Vol. 27$^{III/IV}$, pages 56, 121 ff and 201.

Pyrrolidines: *Beilsteins Handbuch der Organischen Chemie*, Vol. 20$^{III/IV}$, pages 92, 114, 124 and 125.

Pyrrolidinones: *Beilsteins Handbuch der Organischen Chemie*, Vol. 21$^{III/IV}$, pages 3152 ff and 3259 ff.

Indoles: Chem. Abstr. 112, 098378 and Chem. Abstr. 111, 042668.

The compounds of formula Ie

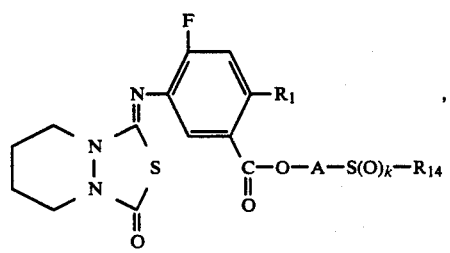

(Ie)

wherein $R_1$, $R_{14}$ and A are as defined under formula I in claim 1 and k is 1 or 2, can also be obtained by oxidising a thioether of formula If

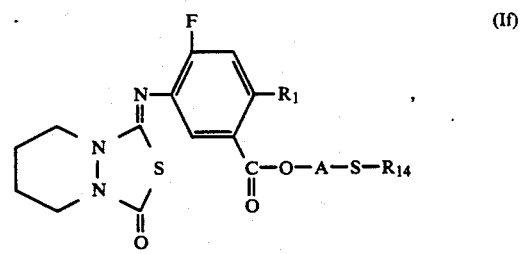

(If)

wherein $R_1$, $R_{14}$ and A are as defined under formula I in claim 1.

The oxidations are preferably carried out in solution at temperatures of from 0° C. to 100° C.

Such oxidations are familiar to the person skilled in the art. They are described inter alia in Houben Weyl, Methoden der Organischen Chemie (Methods of Organic Chemistry), Vol. IX, p 211 ff. A suitable oxidising agent is, in addition to hydrogen peroxide, or peracids, for example m-chloroperbenzoic acid, potassium permanganate in glacial acetic acid.

The starting compounds of formulae II and IV are known or can be prepared analogously to processes known in the literature. For example, the compounds of formula II can be obtained by reacting the corresponding amino-benzoic acid esters of formula V

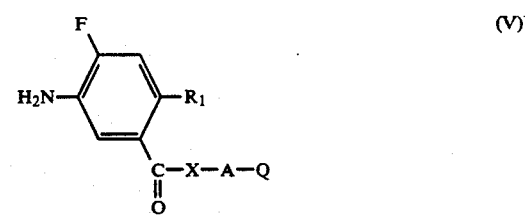

(V)

wherein $R_1$, X, A and Q are as defined under formula I with thiocarbonyl chloride.

The preparation of the starting compounds of formula V is described in EP-A-0 233 151 and EP-A-0 338 987.

The starting compounds of formulae VI and VIII can be prepared analogously to processes known in the literature in accordance with the following scheme:

SCHEME 1

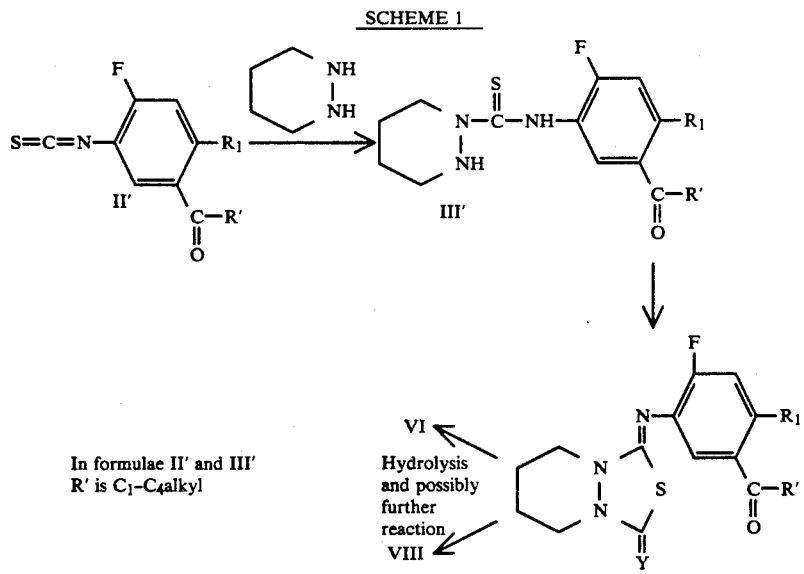

In formulae II' and III'
R' is $C_1-C_4$alkyl

Starting from the ester II', first of all, analogously to the synthesis of the compounds of formula I, the thiourea III' is prepared. This is then cyclised to form the 9-phenylimino-8-thia-1,6-diazabicyclo[4.3.0]nonan-7-one ester. The free acid can be prepared from that ester by hydrolysis. The acid chlorides, bromides, azides or mixed acid anhydrides of formulae VI and VIII are readily obtainable via the acid (R'=OH) in accordance with processes known per se.

The compounds of formula I are generally used successfully at rates of application of from 0.001 to 5 kg/ha, especially from 0.005 to 3 kg/ha. The concentration required to achieve the desired effect can be determined by experiment. It is dependent on the type of action, the stage of development of the cultivated plant and of the weed, and also on the application (place, time, method) and, in dependence on those parameters, can vary within wide limits.

When used at relatively low rates of application, the compounds of formula I are distinguished by growth-inhibiting and selective herbicidal properties, which render them excellently suitable for use in crops of useful plants, especially in cereals, cotton, soybeans, rape, maize and rice, their use as a selective herbicide in cereals (wheat, barley, rye), soybeans and maize, especially soybeans, being preferred.

The invention relates also to herbicidal and plant growth regulating compositions comprising a novel compound of formula I, and to methods of inhibiting plant growth.

Plant growth regulators are substances that bring about agronomically desirable biochemical and/or physiological and/or morphological changes in/to the plant.

The active ingredients present in the compositions according to the invention influence plant growth in different ways depending on the time of application, the concentration, the type of application and the environmental conditions. Plant growth regulators of formula I can, for example, inhibit the vegetative growth of plants. This type of action is valuable in the case of lawn areas, in the cultivation of ornamentals, in fruit plantations, in the case of roadside embankments and in sports fields and industrial sites, but also in the specific inhibition of side-shoots, as in the case of tobacco. In agriculture, inhibition of the vegetative growth of cereals leads, owing to strengthening of the stalk, to reduced lodging, and a similar agronomic effect is achieved in rape, sunflowers, maize and other cultivated plants. Moreover, by inhibiting the vegetative growth it is possible to increase the number of plants per unit area. Another field of application of growth inhibitors is the selective control of cover plants in plantations or widely spaced crops by greatly inhibiting the growth of the cover crops without killing them, so that competition with the main crop is eliminated but the agronomically positive effects, such as erosion prevention, fixing of nitrogen and loose soil structure, are preserved.

A method of inhibiting plant growth is to be understood as being a method of controlling a plant's natural development without changing its life-cycle, as determined by genetic characteristics, in the sense of mutation. The method of regulating growth is applied at a time in the plant's development that has to be determined for each individual case. The compounds of formula I can be applied pre- or post-emergence, for example to the seeds or seedlings, to roots, tubers, stalks, leaves, blossoms or other parts of the plant. This can be done, for example, by applying the compound as such or in the form of a composition to the plants, and/or by treating the plant's nutrient medium (soil).

Various methods and techniques are suitable for the use of the compounds of formula I or of compositions comprising them as herbicides or for regulating plant growth, for example the following:

i) Seed dressing a) Dressing the seeds with an active ingredient formulated as a wettable powder, by shaking in a container until the formulation is uniformly distributed over the surface of the seeds (dry dressing). Up to 4 g of a compound of formula I (in the case of a 50% formulation: up to 8.0 g of wettable powder) are used per 1 kg of seed.

b) Dressing the seeds with an emulsifiable concentrate of the active ingredient or with an aqueous solution of the compound of formula I formulated as a wettable powder according to method a) (wet dressing).

c) Dressing by soaking the seeds for a period of from 1 to 72 hours in a liquor comprising up to 1000 ppm of a compound of formula I and, if desired, subsequently drying the seeds (seed soaking).

Seed dressing or treatment of the germinated seedling are naturally the preferred methods of application because the treatment with the active ingredient is then directed wholly at the target crop. From 4.0 g to 0.001 g of active ingredient are normally used per 1 kg of seed, although, depending on the method employed, which also allows the addition of other active ingredients or micronutrients, amounts that exceed or fall short of the specified concentration limits may be employed (repeat dressing).

ii) Controlled release of active ingredient

A solution of the active ingredient is applied to mineral granule carriers or polymerised granules (urea/formaldehyde) and allowed to dry. If required, a coating may be applied (coated granules), which allows the active ingredient to be released in metered amounts over a specific period of time.

The compounds of formula I are used in unmodified form or, preferably, in the form of compositions together with the adjuvants conventionally employed in formulation technology, and are therefore formulated in known manner e.g. into emulsifiable concentrates, directly sprayable or dilutable solutions, dilute emulsions, wettable powders, soluble powders, dusts, granules, and also encapsulations in e.g. polymer substances. As with the nature of the compositions, the methods of application, such as spraying, atomising, dusting, scattering or pouring, are chosen in accordance with the intended objectives and the prevailing circumstances.

The formulations, i.e. the compositions, preparations or mixtures comprising the compound (active ingredient) of formula I and, where appropriate, a solid or liquid adjuvant, are prepared in known manner, e.g. by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethyl sulfoxide or dimethylformamide, as well as vegetable oils or epoxidised vegetable oils, such as epoxidised coconut oil or soybean oil; or water.

The solid carriers used, e.g. for dusts and dispersible powders, are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable non-sorbent carriers are, for example, calcite or sand. In addition, a great number of pregranulated materials of inorganic or organic nature can be used, e.g. especially dolomite or pulverised plant residues.

Depending on the nature of the compound of formula I to be formulated, suitable surface-active compounds are non-ionic, cationic and/or anionic surfactants having good emulsifying, dispersing and wetting properties. The term "surfactants" will also be understood as comprising mixtures of surfactants.

Both so-called water-soluble soaps and water-soluble synthetic surface-active compounds are suitable anionic surfactants.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained e.g. from coconut oil or tallow oil. Mention may also be made of fatty acid methyltaurin salts.

More frequently, however, so-called synthetic surfactants are used, especially fatty sulfonates, fatty sulfates, sulfonated benzimidazole derivatives or alkylarylsulfonates.

The fatty sulfates or sulfonates are usually in the form of alkali metal salts, alkaline earth metal salts or unsubstituted or substituted ammonium salts and contain a $C_8$–$C_{22}$alkyl radical, which also includes the alkyl moiety of acyl radicals, e.g. the sodium or calcium salt of lignosulfonic acid, of dodecyl sulfate or of a mixture of fatty alcohol sulfates obtained from natural fatty acids. These compounds also comprise the salts of sulfated and sulfonated fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a condensate of naphthalenesulfonic acid and formaldehyde.

Also suitable are corresponding phosphates, e.g. salts of the phosphoric acid ester of an adduct of p-nonylphenol with 4 to 14 mols of ethylene oxide, or phospholipids.

Non-ionic surfactants are preferably polyglycol ether derivatives of aliphatic or cycloaliphatic alcohols, saturated or unsaturated fatty acids and alkylphenols, said derivatives containing 3 to 10 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediaminopolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyethylene glycol ethers, polypropylene/polyethylene oxide adducts, tributylphenoxypolyethoxyethanol, polyethylene glycol and octylphenoxypolyethoxyethanol.

Fatty acid esters of polyoxyethylene sorbitan, e.g. polyoxyethylene sorbitan trioleate, are also suitable non-ionic surfactants.

Cationic surfactants are preferably quaternary ammonium salts which contain, as N-substituent, at least one $C_8$–$C_{22}$alkyl radical and, as further substituents, unsubstituted or halogenated lower alkyl, benzyl or hydroxy-lower alkyl radicals. The salts are preferably in the form of halides, methyl sulfates or ethyl sulfates, e.g. stearyltrimethylammonium chloride or benzyldi(2-chloroethyl)ethylammonium bromide.

The surfactants customarily employed in formulation technology are described inter alia in the following publications:

"McCutcheon's Detergents and Emulsifiers Annual", Mc Publishing Corp., Glen Rock, N.J., 1988;

M. and J. Ash, "Encyclopedia of Surfactants", Vol. I-III, Chemical Publishing Co., N.Y., 1980-1981;

Dr. Helmut Stache, "Tensid-Taschenbuch" (Handbook of Surfactants), Carl Hanser Verlag, Munich/Vienna, 1981.

The agrochemical compositions generally comprise 0.1 to 95%, preferably 0.1 to 80%, of a compound of formula I, 1 to 99.9% of a solid or liquid adjuvant and 0 to 25%, preferably 0.1 to 25%, of a surfactant.

Preferred formulations are composed in particular of the following constituents (%=percentage by weight):

| Emulsifiable concentrates: | |
|---|---|
| active ingredient: | 1 to 20%, preferably 5 to 10% |
| surfactant: | 5 to 30%, preferably 10 to 20% |
| liquid carrier: | 50 to 94%, preferably 70 to 85% |
| Dusts: | |
| active ingredient: | 0.1 to 10%, preferably 0.1 to 1% |
| solid carrier: | 99.9 to 90%, preferably 99.9 to 99% |
| Suspension concentrates: | |
| active ingredient: | 7 to 75%, preferably 10 to 50% |
| water: | 94 to 24%, preferably 88 to 30% |
| surfactant: | 1 to 40%, preferably 2 to 30% |
| Wettable powder: | |
| active ingredient | 0.5 to 90%, preferably 1 to 80% |
| surfactant: | 0.5 to 20%, preferably 1 to 15% |
| solid carrier: | 5 to 99%, preferably 15 to 90% |
| Granulates: | |
| active ingredient: | 0.5 to 30%, preferably 3 to 15% |
| solid carrier: | 99.5 to 70%, preferably 97 to 85%. |

Whereas commercial products will preferably be formulated as concentrates, the end user will normally employ dilute formulations. The formulations can be diluted to a concentration as low as 0.001% active ingredient. The rates of application are normally from 0.001 to 5 kg a.i./ha, preferably from 0.005 to 3 kg a.i./ha.

The compositions may also comprise further auxiliaries such as stabilisers, antifoams, viscosity regulators, binders, tackifiers as well as fertilisers or other active ingredients for obtaining special effects.

The following Examples illustrate the invention.

PREPARATION EXAMPLES

EXAMPLE P1

Preparation of 2-chloro-4-fluoro-5-nitro-benzoic acid (1-methyl-2-methylthio)-ethyl ester

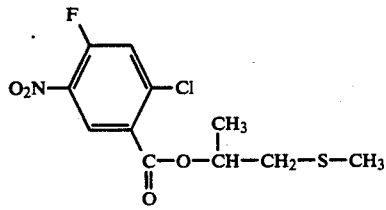

A solution of 20.7 g of 2-chloro-4-fluoro-5-nitrobenzoic acid chloride in 25 ml of ethyl acetate is added dropwise, with stirring, at room temperature to a solution of 9.3 g of methylthiopropan-2-ol und 8.8 g of triethylamine in 100 ml of ethyl acetate. After the addition is complete, the reaction mixture is stirred for a further 7 hours at room temperature, the triethylamine hydrochloride that has formed is filtered off and the filtrate is concentrated in vacuo.

21.4 g of 2-chloro-4-fluoro-5-nitro-benzoic acid (1-methyl-2-methylthio)-ethyl ester are obtained in solid form having a melting point of +47° to +48° C.

EXAMPLE P2

Preparation of 5-amino-2-chloro-4-fluoro-benzoic acid (1-methyl-2-methylthio)-ethyl ester

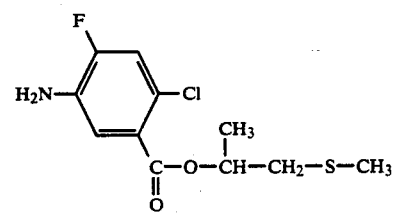

21.4 g of 2-chloro-4-fluoro-5-nitro-benzoic acid (1-methyl-2-methylthio)-ethyl ester obtained in accordance with Example P1 are hydrogenated with hydrogen under normal pressure in 240 ml of tetrahydrofuran at a temperature of 20°-25° C. in the presence of 14 g of Raney nickel catalyst. After the stoichiometric amount of hydrogen has been consumed, the catalyst is separated off and the solution is concentrated by evaporation, yielding 18.6 g of 5-amino-2-chloro-4-fluoro-benzoic acid (1-methyl-2-methylthio)-ethyl ester, $n_D^{22}$ 1.5628.

EXAMPLE P3

Preparation of 2-chloro-4-fluoro-5-isothiocyanato-benzoic acid (1-methyl-2-methylthio)-ethyl ester

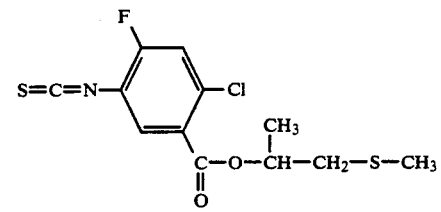

A solution of 4.2 g of the 5-amino-2-chloro-4-fluoro-benzoic acid (1-methyl-2-methylthio)-ethyl ester obtained in accordance with Example P2 in 20 ml of dichloromethane is added dropwise at 25°-30° C. to a suspension of 2.3 g of calcium carbonate, 1.5 ml of thiophosgene, 10 ml of dichloromethane and 10 ml of water. When the evolution of carbon dioxide has ceased, the reaction mixture is stirred at room temperature for 18 hours. After filtration and washing with water, the organic phase is separated off, dried over sodium sulfate and then concentrated by evaporation, yielding 5.4 g of 2-chloro-4-fluoro-5-isothiocyanato-benzoic acid (1-methyl-2-methylthio)-ethyl ester in oily form, which is used in the next reaction step without further purification.

EXAMPLE P4

Preparation of 2-chloro-4-fluoro-5-(1-hexahydropyridazinyl-thiocarbonylamino)-benzoic acid (1-methyl-2-methylthio)-ethyl ester

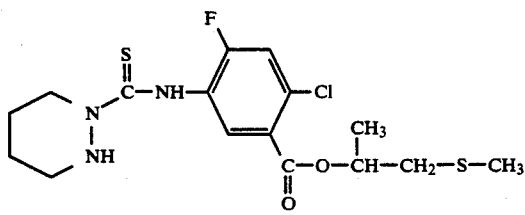

A solution of 4.4 g of the 2-chloro-4-fluoro-5-isothiocyanato-benzoic acid (1-methyl-2-methylthio)-ethyl ester obtained in accordance with Example P3 in 10 ml of toluene is added dropwise, with stirring, at 20°–25° C. to a solution of 1.2 g of hexahydropyridazine in 5 ml of toluene. The reaction mixture is then stirred for 2 hours at room temperature. After concentration by evaporation in vacuo, 5.4 g of 2-chloro-4-fluoro-5-(1-hexahydropyridazinyl-thiocarbonylamino)-benzoic acid (1-methyl-2-methylthio)-ethyl ester are obtained, $n_D^{22}$ 1.6018.

EXAMPLE P5

Preparation of 9-[4-chloro-2-fluoro-5-(1-methyl-2-methylthio-ethoxycarbonyl)-phenylimino]-8-thia-1,6-diazabicyclo[4.3.0]nonan-7-one (Compound No. 1.02)

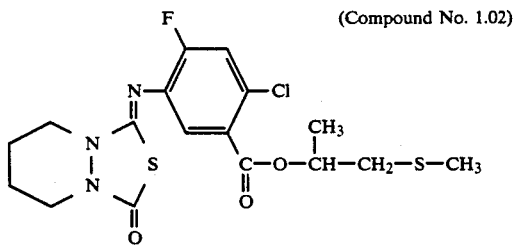

(Compound No. 1.02)

1 ml of a 20% toluene solution of phosgene is added dropwise, with stirring, at a temperature of 0° C. to a solution of 5.2 g of the 2-chloro-4-fluoro-5-(1-hexahydropyridazinyl-thiocarbonylamino)-benzoic acid (1-methyl-2-methylthio)-ethyl ester obtained in accordance with Example P4 and 4 ml of pyridine in 100 ml of dichloromethane. The reaction mixture is then stirred for a further 2 hours and then poured into ice-water. The organic phase is separated off and dried over sodium sulfate. Concentration by evaporation and subsequent purification of the resulting oily product by chromatography yield 3.2 g of 9-[4-chloro-2-fluoro-5-(1-methyl-2-methylthio-ethoxycarbonyl)-phenylimino]-8-thia-1,6-diazabicyclo[4.3.0]nonan-7-one (Compound No. 1.02), $n_D^{22}$ 1.5973.

EXAMPLE P6

Preparation of 2-chloro-4-fluoro-5-nitro-thiolbenzoic acid (methoxycarbonylmethyl) ester

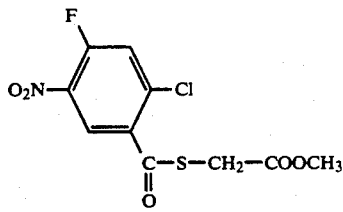

48 g of 2-chloro-4-fluoro-5-nitro-benzoic acid chloride are added dropwise, with stirring, at room temperature to a solution of 20 ml of thioglycolic acid methyl ester in 100 ml of ethyl acetate. Stirring for 18 hours and subsequent evaporation of the solution in vacuo yield 19 g of 2-chloro-4-fluoro-5-nitro-thiolbenzoic acid (methoxycarbonylmethyl) ester in the form of an oil with $n_D^{23}$: 1.5709.

EXAMPLE P7

Preparation of 5-amino-2-chloro-4-fluoro-thiolbenzoic acid (methoxycarbonylmethyl) ester

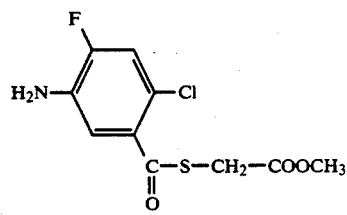

10.4 g of the 2-chloro-4-fluoro-5-nitro-thiolbenzoic acid (methoxycarbonylmethyl) ester obtained in accordance with Example P1 are hydrogenated with hydrogen under normal pressure in 150 ml of tetrahydrofuran at a temperature of 20°–25° C. in the presence of 2 g of Raney nickel catalyst. After the stoichiometric amount of hydrogen has been consumed, the catalyst is separated off and the solution is concentrated by evaporation, yielding 8.6 g of 5-amino-2-chloro-4-fluoro-thiolbenzoic acid (methoxycarbonylmethyl) ester having a melting point of from +88° to +89° C.

EXAMPLE P8

Preparation of 2-chloro-4-fluoro-5-isothiocyanato-thiolbenzoic acid (methoxycarbonylmethyl) ester

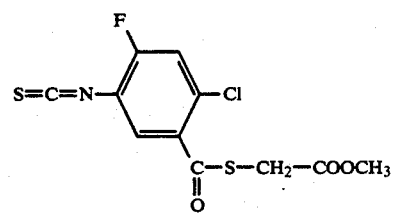

A solution of 3.8 g of the 5-amino-2-chloro-4-fluoro-thiolbenzoic acid (methoxycarbonylmethyl) ester obtained in accordance with Example P2 in 100 ml of dichloromethane is added dropwise at 25°–30° C. to a suspension of 6 g of calcium carbonate, 4 ml of thiophosgene, 20 ml of dichloromethane and 20 ml of water. After the evolution of carbon dioxide has ceased, the mixture is stirred for 18 hours at room temperature. After filtration and washing with water, the organic phase is separated off, dried over sodium sulfate and then concentrated by evaporation, yielding 4.8 g of 2-chloro-4-fluoro-5-isothiocyanato-thiolbenzoic acid (methoxycarbonylmethyl) ester in the form of an oil which is used in the next reaction step without further purification.

EXAMPLE P9

Preparation of 2-chloro-4-fluoro-5-(1-hexahydropyridazinyl-thiocarbonylamino)-thiolbenzoic acid (methoxycarbonylmethyl) ester

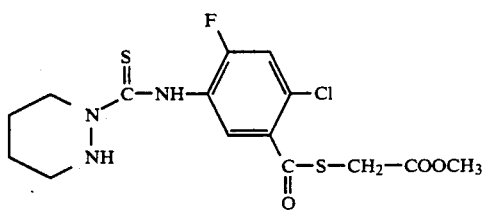

A solution of 4.8 g of 2-chloro-4-fluoro-5-isothiocyanato-thiolbenzoic acid (methoxycarbonylmethyl) ester obtained in accordance with Example P3 in 50 ml of toluene is added dropwise, with stirring, at 20°–25° C. to a solution of 1.4 g of hexahydropyridazine in 20 ml of toluene. Stirring is continued for a further 8 hours at room temperature. Concentration by evaporation in vacuo yields 4.4 g of 2-chloro-4-fluoro-5-(1-hexahydropyridazinyl-thiocarbonylamino)-thiolbenzoic acid (methoxycarbonylmethyl) ester in resinous form.

EXAMPLE P10

Preparation of 9-[4-chloro-2-fluoro-5-(methoxycarbonylmethylthiocarbonyl)-phenylimino]-8-thia-1,6-diazabicyclo[4.3.0-]nonan-7-one (Compound No. 2.13)

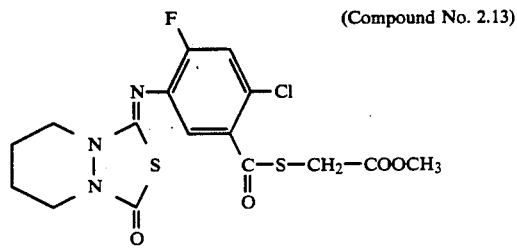

(Compound No. 2.13)

8 ml of a 20% toluene solution of phosgene is added dropwise, with stirring, at a temperature of 0° C. to a solution of 4.4 g of 2-chloro-4-fluoro-5-(1-hexahydropyridazinylthiocarbonylamino)-thiolbenzoic acid (methoxycarbonylmethyl) ester obtained in accordance with Example P4 and 5 ml of pyridine in 10 ml of dichloromethane. The reaction mixture is then stirred for a further 2 hours and then poured into ice-water. The organic phase is separated off and dried over sodium sulfate. Concentration by evaporation and subsequent purification of the resulting oily product by chromatography yield 3 g of 9-[4-chloro-2-fluoro-5-(methoxycarbonylmethylthiocarbonyl)-phenylimino]-8-thia-1,6-diazabicyclo[4.3.0]nonan-7-one (Compound No. 2.13) with $n_D^{19}$ 1.5727.

EXAMPLE P11

Preparation of 9-{4-chloro-2-fluoro-5-[2-(4-methyl-1,3-thiazol-5-yl)-ethoxycarbonyl]phenylimino}-8-thia-1,6-diazabicyclo[4.3.0]nonan-7-one (Compound No. 1.21)

A solution of 3.6 g of 9-[4-chloro-2-fluoro-5-(chlorocarbonyl)-phenylimino]-8-thia-1,6-diazabicyclo[4.3.0]nonan-7-one in 10 ml of methyl acetate is added dropwise, with stirring, at room temperature to a solution of 1.2 ml of 5-(2-hydroxyethyl)-4-methylthiazole and 1.5 ml of triethylamine in 50 ml of methyl acetate. After stirring at room temperature for 12 hours, the precipitated triethylamine hydrochloride is filtered off and the filtrate is concentrated by evaporation, yielding 3.8 g of the title compound in the form of an oil with $n_D^{22}$ 1.6030.

The compounds of Tables 1 and 2 can be prepared analogously to the above Examples and the preparation processes described in the description.

TABLE 1

Compounds of formula I

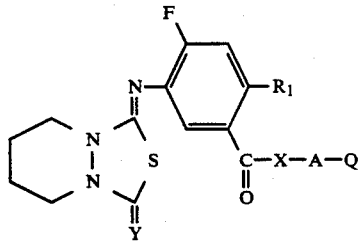

(I)

| Comp. No. | $R_1$ | X | Y | A*) | Q | physic. data |
|---|---|---|---|---|---|---|
| 1.01 | Cl | O | O | —CH—CH$_2$— | SCH$_3$ | |
| 1.02 | Cl | O | O | —CH—CH$_2$—<br>$\|$<br>CH$_3$ | SCH$_3$ | $n_D^{22}$ 1.5973 |
| 1.03 | Cl | O | O | —CH—CH$_2$—<br>$\|$<br>CH$_3$ | SC$_2$H$_5$ | $n_D^{22}$ 1.5765 |
| 1.04 | Cl | O | O | —CH—CH$_2$—<br>$\|$<br>CH$_3$ | SC$_3$H$_7$ | $n_D^{23}$ 1.5825 |
| 1.05 | Cl | O | O | —CH—CH$_2$—<br>$\|$<br>CH$_3$ | SC$_3$H$_7$(iso) | $n_D^{23}$ 1.5768 |
| 1.06 | Cl | O | O | —CH—CH$_2$—<br>$\|$<br>CH$_3$ | SC$_4$H$_9$ | $n_D^{23}$ 1.5691 |
| 1.07 | Cl | O | O | —CH—CH$_2$—<br>$\|$<br>CH$_3$ | SC$_4$H$_9$(sec) | |
| 1.08 | Cl | O | O | —CH—CH$_2$—<br>$\|$<br>CH$_3$ | SC$_4$H$_9$(tert) | |
| 1.09 | Cl | O | O | —CH—CH$_2$—<br>$\|$<br>CH$_3$ | SC$_5$H$_{11}$ | |
| 1.10 | Cl | O | O | —CH—CH$_2$—<br>$\|$<br>CH$_3$ | SC$_6$H$_{13}$ | |
| 1.11 | Cl | O | O | —CH—CH$_2$—<br>$\|$<br>CH$_3$ | SC$_7$H$_{15}$ | |
| 1.12 | Cl | O | O | —CH—CH$_2$—<br>$\|$<br>CH$_3$ | SC$_8$H$_{17}$ | |
| 1.13 | Cl | O | O | —CH—CH$_2$—<br>$\|$<br>CH$_3$ | SC$_9$H$_{19}$ | |
| 1.14 | Cl | O | O | —CH—CH$_2$—<br>$\|$<br>CH$_3$ | SC$_{10}$H$_{21}$ | |
| 1.15 | Cl | O | O | —CH—CH$_2$—<br>$\|$<br>CH$_3$ | SCH$_2$—C$_6$H$_5$ | |

TABLE 1-continued
Compounds of formula I
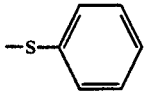
(I)
| Comp. No. | R₁ | X | Y | A*) | Q | physic. data |
|---|---|---|---|---|---|---|
| 1.16 | Cl | O | O | —CH₂—CH₂— |  | $n_D^{22}$ 1.6174 |
| 1.17 | Cl | O | O | —CH—CH₂—<br>　│<br>　CH₃ | 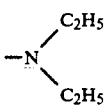 | $n_D^{22}$ 1.5802 |
| 1.18 | Cl | O | O | —CH—CH₂—<br>　│<br>　CH₃ | 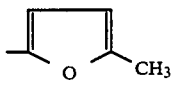 | $n_D^{22}$ 1.5635 |
| 1.19 | Cl | O | O | —CH₂—CH₂— | 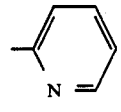 | |
| 1.20 | Cl | O | O | —CH₂—CH₂— | 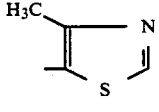 | $n_D^{22}$ 1.6076 |
| 1.21 | Cl | O | O | —CH₂—CH₂— | 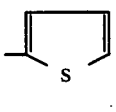 | $n_D^{22}$ 1.6030 |
| 1.22 | Cl | O | O | —CH₂—CH₂— | 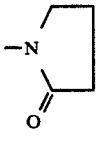 | |
| 1.23 | Cl | O | O | —CH₂—CH₂— | 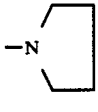 | $n_D^{22}$ 1.5859 |
| 1.24 | Cl | O | O | —CH₂—CH₂— | 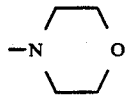 | |
| 1.25 | Cl | O | O | —CH₂—CH₂— | 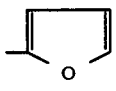 | m.p. 98–99° C. |
| 1.26 | Cl | O | O | —CH—CH₂—<br>　│<br>　CH₃ |  | |

TABLE 1-continued

Compounds of formula I (I)

| Comp. No. | R₁ | X | Y | A*) | Q | physic. data |
|---|---|---|---|---|---|---|
| 1.27 | Cl | O | O | —CH₂—CH₂— | 2-furyl | |
| 1.28 | Cl | O | O | —CH(CH₃)—CH₂— | 1-indolyl | |
| 1.29 | Cl | O | O | —CH₂—CH₂— | 1-pyrazolyl | |
| 1.30 | Cl | O | O | —CH₂—CH₂— | 1-pyrrolyl | |
| 1.31 | Cl | O | O | —CH₂—CH₂— | 1-imidazolyl | |
| 1.32 | Cl | O | O | —CH(CH₃)—CH₂— | —S(O)—CH₂—C₆H₅ | |
| 1.33 | Cl | O | O | —CH(CH₃)—CH₂— | —S(O)₂—CH₂—C₆H₅ | |
| 1.34 | Cl | O | O | —CH(CH₃)—CH₂— | —S(O)₂—C₆H₅ | |
| 1.35 | Cl | O | O | —CH(CH₃)—CH₂— | 1-pyrazolyl | |
| 1.36 | Cl | O | O | —CH(CH₃)—CH₂— | 1-pyrazolyl | |
| 1.37 | Cl | O | O | —CH(CH₃)—CH₂— | 1-imidazolyl | |

TABLE 1-continued

Compounds of formula I

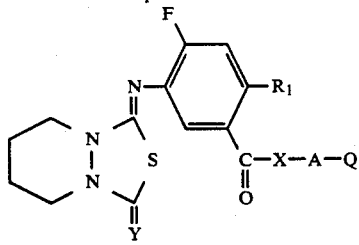

| Comp. No. | R₁ | X | Y | A*) | Q | physic. data |
|---|---|---|---|---|---|---|
| 1.38 | Cl | O | O | —CH—CH₂—<br>    \|<br>   CH₃ | imidazol-1-yl | |
| 1.39 | Cl | O | O | —CH—CH₂—<br>    \|<br>   CH₃ | morpholin-4-yl | |
| 1.40 | Cl | O | O | —CH₂— | —COOCH₂—CH₂—O—CH₃ | |
| 1.41 | Cl | O | O | —CH₂— | —COO—cyclohexyl | |
| 1.42 | Cl | O | O | —CH₂— | —COOCH₂—CH₂—S—CH₃ | |
| 1.43 | Cl | O | O | —CH₂— | —COO—CH—CH₂—N(CH₃)₂<br>        \|<br>       CH₃ | |
| 1.44 | Cl | O | O | —CH—(CH₃)— | —COO—CH₂—CH₂—O—CH₃ | |
| 1.45 | Cl | O | O | —CH—(CH₃)— | —COO—cyclohexyl | |
| 1.46 | Cl | O | O | —CH—(CH₃)— | —COO—CH₂—CH₂—S—CH₃ | |
| 1.47 | Cl | O | O | —CH—(CH₃)— | —COO—CH—CH₂—N(CH₃)₂<br>        \|<br>       CH₃ | |
| 1.48 | Cl | S | O | —CH₂— | —COO—cyclohexyl | $n_D^{28}$ 1.5272 |
| 1.49 | Cl | S | O | —CH₂— | COO—CH₂—CH₂—O—CH₃ | $n_D^{28}$ 1.6038 |
| 1.50 | Cl | O | O | —CH—CH₂—<br>    \|<br>   CH₃ | —S—CH₂—COOC₂H₅ | $n_D^{21}$ 1.5786 |
| 1.51 | Cl | S | O | —CH₂— | —COO—CH(CH₃)—CH₂—O—CH₃ | $n_D^{20}$ 1.5911 |
| 1.52 | Cl | S | O | —CH₂— | —COO—CH₂—CH₂—O—C₂H₅ | $n_D^{20}$ 1.5808 |

TABLE 1-continued

Compounds of formula I (I)

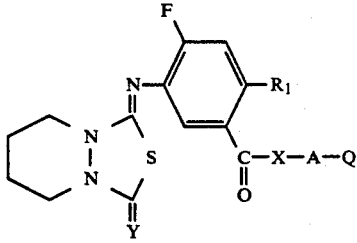

| Comp. No. | R₁ | X | Y | A*) | Q | physic. data |
|---|---|---|---|---|---|---|
| 1.53 | Cl | S | O | CH₃<br>\|<br>—CH— | —COOCH₂—CH₂—O—CH₃ | $n_D^{20}$ 1.5578 |
| 1.54 | Cl | S | O | CH₃<br>\|<br>—CH— | —COOCH₂—CH₂—O—C₂H₅ | $n_D^{20}$ 1.5870 |
| 1.55 | Cl | S | O | CH₃<br>\|<br>—CH— | CH₃<br>\|<br>—COO—CH—CH₂—O—CH₃ | $n_D^{20}$ 1.5796 |
| 1.56 | Cl | O | O | CH₃<br>\|<br>—CHCH₂— | —C₆H₅ (phenyl) | |
| 1.57 | Cl | O | O | —CHCH₂—<br>\|<br>CH₃ | —C₆H₄—Cl (4-chlorophenyl) | $n_D^{22}$ 1.5997 |

*)The alkylene bridge A is bonded to substituents X and Q in the direction of reading (from left to right)

TABLE 2

Compounds of formula I (I)

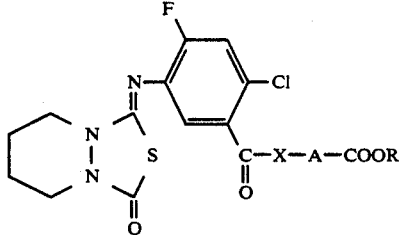

| Comp. No. | X | A | R | physic. data |
|---|---|---|---|---|
| 2.01 | O | —CH₂— | —COOCH₃ | $n_D^{25}$ 1,5853 |
| 2.02 | O | —CH₂— | —COOC₂H₅ | $n_D^{22}$ 1,5803 |
| 2.03 | O | —CH₂— | —COOC₅H₁₁(n) | |
| 2.04 | O | —CH(CH₃)— | —COOCH₃ | mp. 87–88° C. |
| 2.05 | O | —CH(CH₃)— | —COOC₂H₅ | |
| 2.06 | O | —CH(CH₃)— | —COO—C₃H₇ | |
| 2.07 | O | —CH(CH₃)— | —COOC₃H₇(i) | |
| 2.08 | O | —CH(CH₃)— | —COOC₄H₉ | |
| 2.09 | O | —CH(CH₃)— | —COOC₄H₉(i) | |
| 2.10 | O | —CH(CH₃)— | —COOC₄H₉(s) | |
| 2.11 | O | —CH(CH₃)— | —COOC₄H₉(t) | |
| 2.12 | O | —CH(CH₃)— | —COOC₅H₁₁ | |
| 2.13 | S | —CH₂— | —COOCH₃ | $n_D^{19}$ 1,5727 |
| 2.14 | S | —CH₂— | —COOC₂H₅ | $n_D^{22}$ 1,6118 |
| 2.15 | S | —CH₂— | —COOC₃H₇ | |
| 2.16 | S | —CH₂— | —COOC₃H₇ | |
| 2.17 | S | —CH₂— | —COOC₄H₉(i) | |
| 2.18 | S | —CH₂— | —COOC₄H₉(s) | |
| 2.19 | S | —CH₂— | —COOC₄H₉(tert) | |
| 2.20 | S | —CH₂— | —COOC₄H₉ | $n_D^{22}$ 1.5758 |
| 2.21 | S | —CH(CH₃)— | —COOCH₃ | $n_D^{22}$ 1.6009 |
| 2.22 | S | —CH(CH₃)— | —COOC₂H₅ | |
| 2.23 | S | —CH(CH₃)— | —COOC₃H₇ | |

TABLE 2-continued

Compounds of formula I (I)

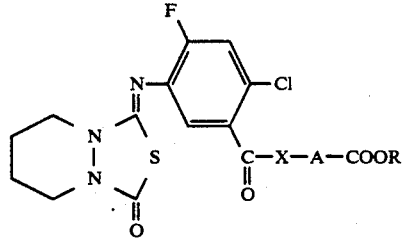

| Comp. No. | X | A | R | physic. data |
|---|---|---|---|---|
| 2.24 | S | —CH(CH₃)— | —COOC₃H₇(iso) | |
| 2.25 | S | —CH(CH₃)— | —COOC₄H₉ | |
| 2.26 | S | —CH(CH₃)— | —COOC₄H₉(iso) | |
| 2.27 | S | —CH(CH₃)— | —COOC₄H₉(sec) | |
| 2.28 | S | —CH(CH₃)— | —COOC₄H₉(tert) | |

FORMULATION EXAMPLES

EXAMPLE F1

Formulation EXAMPLES for active ingredients of formula I (throughout, percentages are by weight)

| a) Wettable powders | a) | b) | c) |
|---|---|---|---|
| Compound no. 1.02 | 20% | 50% | 0.5% |
| sodium lignosulfonate | 5% | 5% | 4% |
| sodium laurylsulfate | 3% | — | — |
| sodium diisobuylnaphthalene-sulfonate | — | 6% | 6% |
| octylphenol polyethylene glycol ether | — | 2% | 2% |

-continued

| a) Wettable powders | a) | b) | c) |
|---|---|---|---|
| (7-8 mols of ethylene oxide) | | | |
| highly dispersed silicic acid | 5% | 27% | 27% |
| kaolin | 67% | 10% | — |
| sodium chloride | — | — | 59.5% |

The active ingredient is thoroughly mixed with the adjuvants and the mixture is thoroughly ground in a suitable mill, affording wettable powders which can be diluted with water to give suspensions of the desired concentration.

| b) Emulsifiable concentrate | a) | b) |
|---|---|---|
| compound no. 1.02 | 10% | 1% |
| octylphenol polyethylene glycol ether (4-5 mols of ethylene oxide) | 3% | 3% |
| calcium dodecylbenzenesulfonate | 3% | 3% |
| castor oil polyglycol ether (36 mols of ethylene oxide) | 4% | 4% |
| cyclohexanone | 30% | 10% |
| xylene mixture | 50% | 79% |

Emulsions of any required concentration can be obtained from this concentrate by dilution with water.

| c) Dusts | a) | b) |
|---|---|---|
| compound no. 1.02 | 0.1% | 1% |
| talcum | 99.9% | — |
| kaolin | — | 99% |

Ready-for-use dusts are obtained by mixing the active ingredient with the carrier and grinding the mixture in a suitable mill.

| d) Extruder granules | a) | b) |
|---|---|---|
| compound no. 1.02 | 10% | 1% |
| sodium lignosulfonate | 2% | 2% |
| carboxymethylcellulose | 1% | 1% |
| kaolin | 87% | 96% |

The active ingredient is mixed and ground with the adjuvants, and the mixture is moistened with water. The mixture is extruded and then dried in a stream of air.

| e) Coated granules | | |
|---|---|---|
| compound no. 1.02 | | 3% |
| polyethylene glycol (mol. wt. 200) | | 3% |
| kaolin | | 94% |

The finely ground active ingredient is uniformly applied, in a mixer, to the kaolin moistened with polyethylene glycol. Non-dusty coated granules are obtained in this manner.

| f) Suspension concentrate | a) | b) |
|---|---|---|
| compound no. 1.02 | 40% | 5% |
| ethylene glycol | 10% | 10% |
| nonylphenol polyethylene glycol ether (15 mols of ethylene oxide) | 6% | 1% |
| sodium lignosulfonate | 10% | 5% |
| carboxymethylcellulose | 1% | 1% |
| 37% aqueous formaldehyde solution | 0.2% | 0.2% |
| silicone oil in the form of a 75% aqueous emulsion | 0.8% | 0.8% |

-continued

| f) Suspension concentrate | a) | b) |
|---|---|---|
| water | 32% | 77% |

The finely ground active ingredient is intimately mixed with the adjuvants, giving a suspension concentrate from which suspensions of any desired concentration can be obtained by dilution with water.

| g) Salt solution | |
|---|---|
| compound no. 1.02 | 5% |
| isopropylamine | 1% |
| octylphenol polyethylene glycol ether (78 mols of ethylene oxide) | 3% |
| water | 91% |

BIOLOGICAL EXAMPLES

EXAMPLE B1

Preemergence herbicidal action

In a greenhouse, immediately after the test plants have been sown in seed trays, the surface of the soil is treated with an aqueous spray mixture in an amount corresponding to a rate of application of 250 g of test compound/hectare. The seed trays are kept in the greenhouse at 22°-25° C. and 50-70% relative humidity.

After 3 weeks, the herbicidal action is evaluated according to a scale of nine ratings (1=total damage, 9=no action) in comparison with an untreated control group.

Ratings of from 1 to 4 (especially from 1 to 3) indicate good to very good herbicidal action. Ratings of from 6 to 9 (especially from 7 to 9) indicate good tolerance (especially in cultivated plants).

The compounds of Tables 1 and 2 exhibit pronounced herbicidal activity in this test. The results for the compound of formula 1.54 are summarised in Table 3:

TABLE 3

| Test plant | Application rate [g/ha] | |
|---|---|---|
| | 250 | 125 |
| Wheat | 7 | 9 |
| Maize | 8 | 9 |
| Sorghum | 8 | 9 |
| Rice | 7 | 9 |
| Soybeans | 9 | 9 |
| Abutilon | 1 | 1 |
| Amaranthus ret. | 1 | 2 |
| Chemopodium | 1 | 1 |
| Solanum n. | 1 | 1 |
| Chrysanthe. leuc. | 1 | 1 |
| Viola tricolor | 1 | 1 |
| Veronica Sp. | 1 | 1 |

EXAMPLE B2

Postemergence herbicidal action (contact herbicide)

A number of weeds, both monocotyledonous and dicotyledonous, are sprayed postemergence (in the 4- to 6-leaf stage) with an aqueous active ingredient dispersion at a rate of 30-1000 g of test compound per hectare and kept at 24°-26° C. and 45-60% relative humidity. After 15 days, the herbicidal action is evaluated according to a scale of nine ratings (1=total damage, 9=no action) in comparison with an untreated control group. Individual results are summarised in Tables 4, 5 and 6:

TABLE 4

| | Herbicidal action of compound No. 1.02: | | | |
|---|---|---|---|---|
| | Application rate [g/ha] | | | |
| Pflanze | 1000 | 500 | 250 | 125 |
| Abutilon | 1 | 1 | 1 | 1 |
| Sida spinosa | 1 | 1 | 1 | 1 |
| Xanthium Sp. | 1 | 1 | 1 | 1 |
| Amaranthus ret. | 1 | 1 | 1 | 1 |
| Chenopodium Sp. | 1 | 1 | 1 | 1 |
| Solanum nigrum | 1 | 1 | 1 | 1 |
| Ipomoea | 1 | 1 | 1 | 1 |
| Sinapis | 1 | 1 | 1 | 1 |
| Stellaria | 1 | 1 | 1 | 1 |
| Chrysanthe. leuc. | 1 | 1 | 1 | 1 |
| Galium aparine | 1 | 1 | 1 | 1 |
| Viola tricolor | 1 | 1 | 1 | 1 |
| Veronica Sp. | 1 | 1 | 1 | 1 |

TABLE 6

| | Herbicidal action of compound No. 1.54 | |
|---|---|---|
| | Application rate [g/ha] | |
| Test plant | 250 | 125 |
| Barley | 8 | 9 |
| Wheat | 9 | 9 |
| Rice | 9 | 9 |
| Abutilon | 1 | 1 |
| Sida spinosa | 1 | 1 |
| Xanthium sp. | 1 | 1 |
| Chemopodium | 1 | 1 |
| Solanum n. | 1 | 1 |
| Ipomoea | 1 | 1 |
| Sinapis | 1 | 1 |
| Chrysanthe. leuc. | 1 | 1 |
| Viola tricolor | 1 | 1 |

EXAMPLE B3

Herbicidal action in wild rice (paddy rice)

The weeds Echinochloa crus galli and Monocharia vag., which occur in water, are sown in plastic beakers (surface: 60 cm², volume: 500 ml). After sowing, the beakers are filled with water up to the surface of the soil. 3 days after sowing, the water level is increased to slightly above the soil surface (3-5 mm). Application is effected 3 days after sowing by spraying the beakers with the test compounds. The rate of application corresponds to a concentration of 250 g of active ingredient per hectare. The beakers are then kept in the greenhouse under optimum growth conditions for rice weeds, i.e. at 25°-30° C. and at high humidity.

The evaluation of the tests takes place 3 weeks after application. The compounds of Tables 1 and 2 damage the weeds but not the rice.

EXAMPLE B4

Growth inhibition of tropical cover crops

The test plants Centrosema pubescens and Psophocarpus palustris are propagated by means of cuttings in 4 cm peat pots containing earth (45%), peat (45%) and Zonolite (10%). The cuttings are raised in a greenhouse at a day temperature of 27° C. and a night temperature of 23° C. The plants are illuminated for at least 14 hours/day with an intensity of at least 7000 lux.

About 50 days after the cuttings are taken, they are transplanted into 13 cm pots, 4–5 plants/pot. After a further 60 days, the plants are cut back to a height of about 15 cm and treated by spraying with an aqueous spray mixture at a concentration of 0.1 to 300 g of active ingredient/ha (usually as a 25% formulation). The amount of water applied is about 200 l/ha.

4 weeks after application, the weight of the new growth is determined and expressed as a percentage of the average of the untreated controls. The necrotic damage is given as a percentage of the total leaf area.

The new growth on the treated plants is markedly less than that on the untreated controls.

EXAMPLE B5

Growth regulation of soybeans

Test plants of the Williams variety are sown in 11 cm clay pots containing earth (45%), peat (45%) and Zonolite (10%) and are raised in a climatic chamber at a day temperature of 24° C. and a night temperature of 19° C. The plants are illuminated for 16 hours per day with an intensity of about 350 micro-einsteins.

About 24 days after sowing, the plants are transplanted into 18 cm pots, 2 plants/pot. After a further 12 days, when the plants are in the 5–6 trefoil leaf stage, the test compound is applied at a concentration of 0.1 to 300 g of active ingredient/ha, usually as a 25% formulation and in an aqueous spray mixture. The amount of water applied is about 200 l/ha.

Evaluation is made about 4 weeks after application. The height of the new growth is measured and expressed as a percentage of the average of the untreated controls. The necrotic damage is given as a percentage of the total leaf area.

The treated plants exhibit markedly less new growth than do the untreated controls.

EXAMPLE B6

Growth inhibition of cereals

Test plants (summer barley of the Iban variety) are sown in 15 cm plastic pots containing sterile earth and raised in a climatic chamber at a day temperature of 10°-15° C. and a night temperature of 5°-10° C. The plants are illuminated for 13.5 hours per day with an intensity of about 25000 lux.

About 34 days after sowing, and after the plants have been thinned out to 4 plants/pot, the test compound is applied at a concentration of 0.1 to 300 g of active ingredient/ha, usually as a 25% formulation and in an aqueous spray mixture. The amount of water applied is about 500 l/ha. After application, the plants are placed in a greenhouse at a day temperature of at least 10° C. They are illuminated for at least 13.5 hours/day.

Evaluation is made about 28 days after the treatment. The height of the new growth is expressed as a percentage of the average of the untreated controls. The necrotic damage is given as a percentage of the total leaf area.

The treated plants exhibit a reduction in new growth in comparison with untreated controls.

EXAMPLE B7

Growth inhibition of grasses

A mixture of grasses (e.g. Poa, Festuca, Lolium, Bromus, Cynosurus) and clover (Trifolium pratense/repens) is sown in 15 cm plastic pots containing sterile earth and the plants are raised in a greenhouse at a day temperature of 21° C. and a night temperature of 17° C. The plants are illuminated for 13.5 hours/day with an intensity of at least 7000 lux. The emergent plants are cut back weekly to a height of about 6 cm. About 42 days after sowing and 1 day after the last cut, the test compound is applied at a concentration of 0.1 to 300 g of active ingredient/ha, usually as a 25% formulation and in an aqueous spray mixture. The amount of water applied is about 500 l/ha.

Evaluation is made about 3 weeks after treatment. The height of the new growth is measured and expressed as a percentage of the average of the untreated controls. The necrotic damage is given as a percentage of the total leaf area.

The tested compounds of Tables 1 and 2 effect a reduction in new growth in comparison with untreated controls.

What is claimed is:

1. A compound of formula Ib,

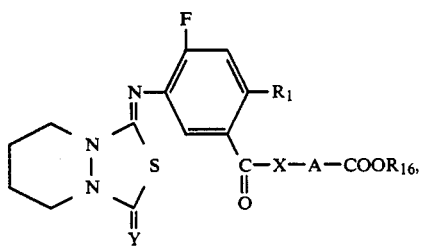

wherein
$R_1$ is halogen;
Y is oxygen;
X is oxygen or sulfur;
A is a $C_1$–$C_2$alkylene chain; and
$R_{16}$ is $C_1$–$C_4$alkoxy-$C_1$–$C_4$alkyl; or $C_1$–$C_4$alkylthio-$C_1$–$C_4$alkyl.

2. A compound of formula Ic,

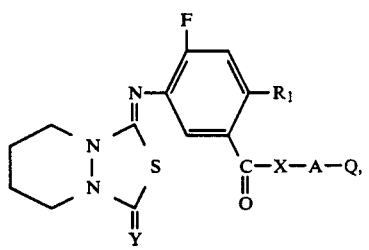

wherein
Y is oxygen;
X is oxygen; or sulfur;
$R_1$ is chlorine;
A is a $C_1$–$C_2$alkylene bridge; and
Q is pyridin-2-yl, 1,3-thiazol-5-yl, thiophen-2-yl, pyrrolidin-2-on-1-yl, pyrrolidin-1-yl, morpholin-4-yl, furan-2-yl, indol-1-yl, pyrrol-1-yl, imidazol-1-yl, pyrazol-1-yl and 1,2,4-triazol-1-yl, which is unsubstituted or substituted once or twice by halogen, $C_1$–$C_4$alkyl, $C_1$–$C_3$haloalkyl, $C_1$–$C_3$alkoxy, $C_1$–$C_3$haloalkoxy, $C_1$–$C_3$dialkylamino or hydroxy.

3. A compound of formula Id

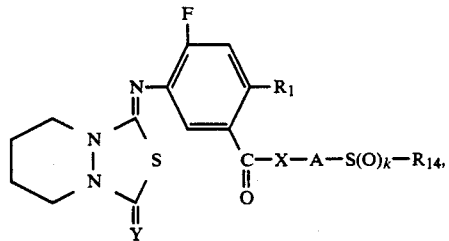

wherein
Y is oxygen;
X is oxygen; or sulfur;
$R_1$ is chlorine;
A is a $C_2$–$C_4$alkylene bridge;
k is 0;
$R_{14}$ is $C_1$–$C_{10}$alkyl;

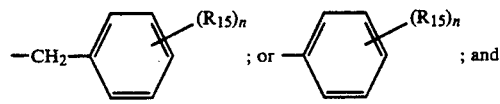

$R_{15}$ is $C_1$–$C_4$alkyl; halogen; or $C_1$–$C_4$alkoxy, and n is 0; 1; 2; or 3.

4. A compound according to claim 1 selected from the group consisting of
9-[4-chloro-2-fluoro-5-(2-methoxy-ethoxycarbonylmethylthiocarbonyl)-phenylimino]-8-thia-1,6-diazabicyclo[4.3.0]nonan-7-one,
9-[4-chloro-2-fluoro-5-(2-methoxy-1-methyl-ethoxycarbonylmethylthiocarbonyl)-phenylimino]-8-thia-1,6-diazabicyclo[4.3.0]nonan-7-one,
9-[4-chloro-2-fluoro-5-(2-methoxy-1-methyl-ethoxycarbonyl-1-ethylthiocarbonyl)-phenylimino]-8-thia-1,6-diazabicyclo[4.3.0]nonan-7-one,
9-[4-chloro-2-fluoro-5-(2-methoxy-ethoxycarbonyl-1-ethylthiocarbonyl)-phenylimino]-8-thia-1,6-diazabicyclo[4.3.0]nonan-7-one and
9-[4-chloro-2-fluoro-5-(2-ethoxy-ethoxycarbonylmethylthiocarbonyl)-phenylimino]-8-thia-1,6-diazabicyclo[4.3.0]nonan-7-one.

5. A compound according to claim 2 selected from the group consisting of
9-{4-chloro-2-fluoro-5-[2-(4-methyl-thiazol-5-yl)-ethoxycarbonyl]-phenylimino}-8-thia-1,6-diazabicyclo[4.3.0]nonan-7-one and 9-{4-chloro-2-fluoro-5-[2-(pyridin-2-yl)-ethoxycarbonyl]phenylimino}-8-thia-1,6-diazabicyclo[4.3.0]nonan-7-one.

6. A compound according to claim 3 selected from the group consisting of
9-[4-chloro-2-fluoro-5-(2-methylthio-1-methylethoxycarbonyl)-phenylimino]-8-thia-1,6-diazabicyclo[4.3.0]nonan-7-one,
9-[4-chloro-2-fluoro-5-(2-ethylthio-1-methylethoxycarbonyl)-phenylimino]-8-thia-1,6-diazabicyclo[4.3.0]nonan-7-one,
9-[4-chloro-2-fluoro-5-(2-propylthio-1-methylethoxycarbonyl)-phenylimino]-8-thia-1,6-diazabicyclo[4.3.0]nonan-7-one,
9-[4-chloro-2-fluoro-5-(2-isopropylthio-1-methylethoxycarbonyl)-]-8-thia-1,6-diazabicyclo[4.3.0]nonan-7-one,
9-[4-chloro-2-fluoro-5-(2-n-butylthio-1-methylethoxycarbonyl)-phenylimino]-8-thia-1,6-diazabicyclo[4.3.0]nonan-7-one, 9-[4-chloro-2-fluoro-5-(2-phenylthio-ethoxycarbonyl)-phenylimino]-8-thia-1,6-diazabicyclo[4.3.0]nonan-7-one and 9-[4-chloro-2-fluoro-5-(2-p-chlorophenylthio-1-methyl-ethoxycarbonyl)-phenylimino]-8-thia-1,6-diazabicyclo[4.3.0]nonan-7-one.

7. A composition comprising at least a herbicidally effective amount of a compound of formula Ib according to claim 1 and an agrochemically acceptable carrier.

8. A method of controlling undesirable plant growth, which comprises applying to the plants or to the locus thereof a herbicidally effective amount of a compound of formula Ib of claim 1.

9. A composition comprising at least a herbicidally effective amount of a compound of formula Ic according to claim 2 and an agrochemically acceptable carrier.

10. A method of controlling undesirable plant growth, which comprises applying to the plants or to the locus thereof a herbicidally effective amount of a compound of formula Ic of claim 2.

11. A composition comprising at least a herbicidally effective amount of a compound of formula Id according to claim 3 and an agrochemically acceptable carrier.

12. A method of controlling undesirable plant growth, which comprises applying to the plants or to the locus thereof a herbicidally effective amount of a compound of formula Id of claim 3.

* * * * *